United States Patent [19]

Ford

[11] 4,367,405
[45] Jan. 4, 1983

[54] BOTTLE INSPECTION APPARATUS

[75] Inventor: Geoffrey E. Ford, Bedford, England

[73] Assignee: TI Fords Limited, Kempston, England

[21] Appl. No.: 252,187

[22] Filed: Apr. 8, 1981

[51] Int. Cl.[3] ............................................. G01N 21/32
[52] U.S. Cl. ................................ 250/223 B; 209/526; 356/240
[58] Field of Search .................... 250/223 B; 356/240; 209/524, 526

[56] References Cited

U.S. PATENT DOCUMENTS 4,025,201  5/1977  Deane ........................ 250/223 B X Primary Examiner—David C. Nelms
Assistant Examiner—Darwin R. Hostetter
Attorney, Agent, or Firm—Brisebois & Kruger

[57] ABSTRACT

The invention relates to an apparatus for inspecting the side walls of transparent bottles for the detection of dirt or foreign bodies therein. The inspection is effected by projecting a plurality of images of the side walls of a bottle, as viewed from at least two different directions in plan, on to at least one integrated circuit device comprising an array of photodiodes arranged in a plurality of rows in combination with means to interrogate each diode in turn, along each row in turn, to provide a video signal comprising a sequence of electrical signals corresponding to the light energy each diode has received. The two optical paths are so folded that over part of their lengths they are parallel and vertical, thus enabling both path lengths to be varied simultaneously by a common adjustment means, thereby to shorten or lengthen the object distance to obtain the appropriate magnification over a range of bottle sizes and make full use of the potential resolution of the photodiode array.

3 Claims, 4 Drawing Figures

BOTTLE INSPECTION APPARATUS

This invention relates to apparatus, herein referred to as bottle inspection apparatus, for the detection of dirt or foreign bodies in transparent bottles or other containers (herein referred to as "bottles") before they are filled and offered for sale, particularly in bottles such as milk or beer bottles which are re-used after washing. The inspection apparatus may detect dirt or foreign bodies lying in the base area of empty bottles, so-called "base inspection". However, many foreign bodies, such as mould growths, cement or paint splashes which can adhere to the sides of a bottle, are not detected by base inspection and can only be detected by inspecting the side walls of the bottles, so-called "side inspection".

RELATED CASE

This application is a continuation-in-part of my co-pending Appln. Ser. No. 947,547 filed Oct. 2, 1978, now U.S. Pat. No. 4,280,624 which describes a bottle inspection apparatus in which images of the side walls of a diffusely illuminated bottle, as viewed from at least two different directions in plan, are projected on to at least one integrated circuit device comprising an array of photodiodes arranged in a plurality of rows in combination with means to interrogate each diode in turn, along each row in turn, to provide a video signal comprising a sequence of electrical signals corresponding to the light energy each diode has received. The video signal is differentiated and unwanted signals outside of the limits of the side walls to be inspected are gated out, whereby to generate a video output pulse representative of dirt in the bottles. This output pulse can be used to control the rejection of faulty bottles from the bottling line.

With such an apparatus as therein described, it is preferable to make the length of the optical path from the bottle to the lens, that is the object distance, at least five times the height of the bottle so that the near and far sides of the bottle are both reasonably in focus and so that the minimum object size detectable on the near and far sides is approximately the same and to ensure that the illumination over the area of the array is reasonably uniform. A wide angle of view with short object distances will produce appreciable fall off in illumination at the edges of the field.

This requirement leads to a large area in plan being required for the optical system even when the optical path is, as described therein, folded by mirrors.

SUMMARY OF THE INVENTION

The present invention provides bottle side-inspection apparatus which not only reduces the area in plan of the optical system for achieving the above desiderata but which also enables the apparatus to be adjusted for inspecting a range of bottle sizes, say from capacities of 24 centiliters to 2 liters, while utilizing the full potential resolution of the photodiode array.

It will be understood that if the dimensions of the optical path and the lens focal length are chosen so that the image of a large bottle on the photodiode array just fills it, a smaller bottle will produce a correspondingly smaller image and will not utilize the potential resolution of the array. To achieve this the image of the smaller bottle must be enlarged to about the same size as that of the larger bottle. While this can be achieved by employing a variable focal length lens, such as a zoom lens, this is expensive. If a simple lens be used the object distance must be varied, which involves changing the position of both pairs of mirrors 15,17 and 16,18 in the embodiment shown in the aforesaid specification, and also the position of the array 19 and beam splitter 12, which would require a very complicated adjustment procedure. This invention dispenses with this complexity while at the same time reducing the floor area occupied by the apparatus.

According to this invention the machine described in the aforesaid specification has its two optical paths so folded that over part of their lengths they are parallel and vertical, thus reducing the area, in plan, required to accommodate the necessary optical path lengths and also enabling both path lengths to be varied simultaneously by a common adjustment means to extend or shorten the object distance to obtain the appropriate magnification over a range of bottle sizes to make full use of the potential resolution of the photodiode array while using a lens of fixed focal length with a conventional, e.g. helical, focussing adjustment.

DESCRIPTION OF THE INVENTION

Figure 1:
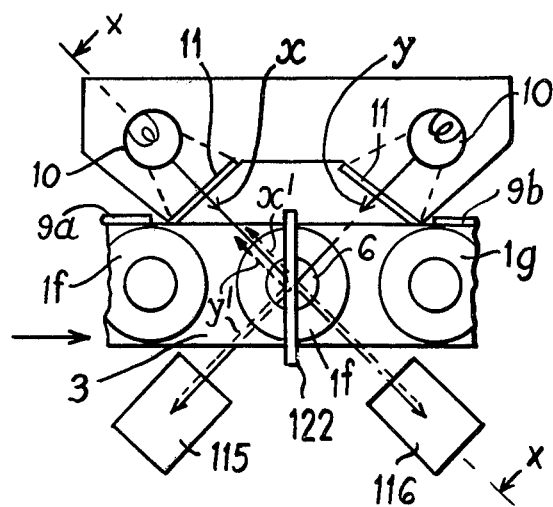
FIG. 1 is a fragmentary plan view of the inspection station portion illustrated in FIG. 1 of my aforesaid co-pending application Ser. No. 947,547, as modified according to this invention, the overhead components, except the semi-reflecting mirror, being omitted.
Figure 2:
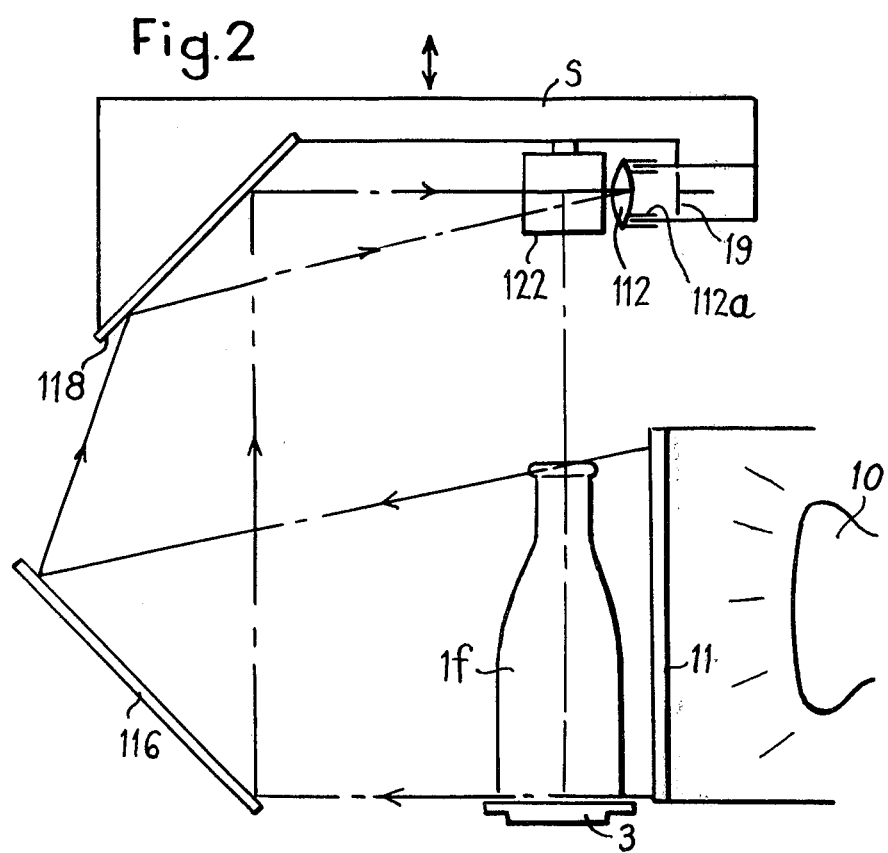
FIG. 2 is a vertical section along the line X—X in FIG. 1, on an enlarged scale.

To avoid repetition the present invention will only be described insofar as it differs from the apparatus described in the aforesaid specification to which reference should be made for a full understanding of this invention. In this specification the same references will be used as are used for the same parts in the earlier specification.

As in the previous machine, the bottle 1f in the centre 6 of the inspection station is illuminated in two directions x, y at right angles by two lamps 10 through light diffusing screens 11 positioned in front of the respective lamps. The light along each viewing direction x, y is reflected by respective mirrors 116, 115 each disposed at 45° to the vertical. The resulting reflected beams are substantially vertical in direction and therefore substantially parallel to each other.

The two vertical beams of light are reflected by two further mirrors 118, 117 respectively, disposed directly above the respective mirrors 116, 115 at 45° to the vertical so that reflected light beams therefrom (indicated by dotted lines x', y' in FIG. 1) are directed back into a substantially horizontal plane along intersecting paths. Close to the point of intersection, directly above the vertical axis of the bottle 1f at the centre of the inspection station in the embodiment shown, is a semi-reflecting mirror or beam splitter cube 122 which reflects one of the beams y' parallel to the other light beam x' so that both may be focussed by a lens 112 on to the photodiode array 19. The angles of the various mirrors are adjusted so that the two images of the bottle lie side-by-side and spaced apart on the photodiode array 19, and such that the lowest part of the body of the bottle will be inspected without obstruction from the bottle base of the conveyor 3.

The upper mirrors 117, 118, the semi-reflecting mirror or beam splitter 122, the lens 112 and the array 119 are carried on a common support S which is mounted for movement up and down, as indicated by the arrows, so that the object distance of the lens 112 may be varied easily, thus enabling the magnification of the lens to be made appropriate to the bottle height. The lens 112 is provided with a focussing mount 112a so that the bottle may be imaged sharply over a range of object distances. Associated circuitry may also be carried by the support S.

According to a further modification, each bottle may be inspected firstly in one direction at a first position in the inspection station and then in the other direction, at right angles to the first direction, at a subsequent position in the inspection station. Two different bottles may be inspected simultaneously in one of said two directions respectively, while being advanced continuously through the inspection station.

Figure 3:
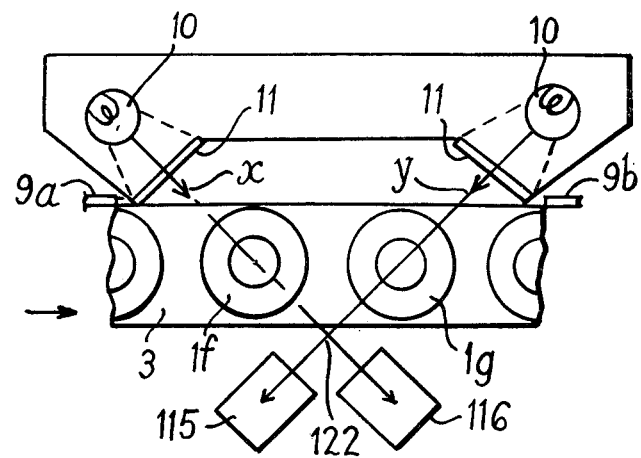
FIGS. 3 and 4 are fragmentary plan views, similar to FIG. 1, of modified constructions in which a bottle is inspected in two directions at right angles to each other at different positions or inspecting locations in the inspection station.

FIG. 3 shows such a modification in which successive bottles, e.g. 1g and 1f, moving continuously in predetermined spaced relationship on the conveyor 3 are simultaneously illuminated in the y and x directions respectively by the two diffuse light sources 10, 11. In this embodiment the point of intersection 122 of the reflected upper horizontal beams, where the semi-reflecting mirror or beam splitter is located, is to the side of the bottles remote from the light sources.

Figure 4:
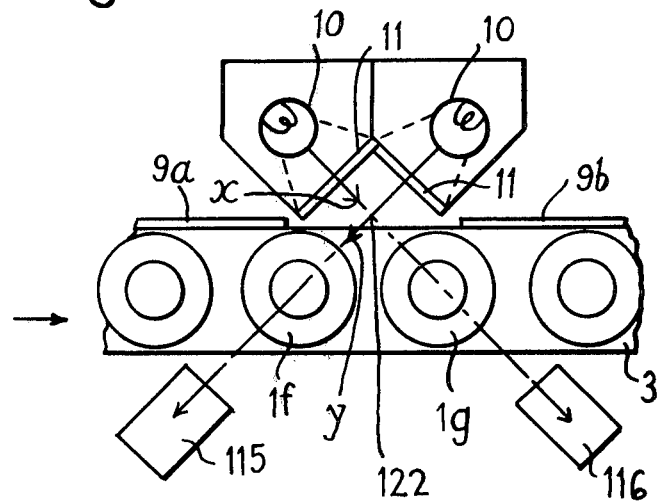

FIG. 4 shows a modification of FIG. 3 in which the bottle 1g is illuminated in the x direction and the following bottle 1f is illuminated in the y direction. In this modification the point of intersection 122 of the upper horizontal beams is to the side of the bottles adjacent the light sources.

With the arrangements of FIGS. 3 and 4, images of two different bottles are simultaneously projected side-by-side on to the photodiode array 19.

I claim:

1. Apparatus for inspecting the side walls of transparent or translucent bottles for the detection of dirt or foreign bodies, comprising means for diffusely illuminating the side walls of a bottle to be inspected while it is moving through an inspection station, means for projecting, while the bottle is so illuminated, a plurality of images of the side walls of the bottle, as viewed from at least two different horizontal directions, on to at least one device whereby to generate signal pulses representative of dirt or foreign bodies in the bottle, means for folding the optical paths along which the rays illuminating the bottle pass between the bottle and lens means which forms the images on to said at least one device, so that each optical path extends vertically and substantially parallel to the other over a part of its length, and a common adjustment to change the lengths of said parts of the optical paths to a desired object distance, said lens being of fixed focal length and provided with focussing adjustment means.

2. Apparatus according to claim 1, including a conveyor for moving the bottles to be inspected, in spaced apart relation and supported only by their bases resting on the conveyor, through the inspection station, said at least one device on which the plurality of images of the side walls of the bottle are projected comprising at least one integrated circuit device comprising an array of photodiodes arranged in a plurality of rows with a plurality of diodes in each row in combination with array scanner means cyclically to scan the array and interrogate each diode in turn, along each row in turn, to provide a video signal comprising a sequence of electrical signals corresponding to the light energy each diode has received, and means for feeding said video signal to electric circuit means including means for differentiating said video signal and means fo gating-out unwanted signals outside the limits of the images of the side walls of the bottle to be inspected whereby to generate differentiated signal pulses representative of dirt or foreign bodies in the bottle.

3. Apparatus according to claim 1 or 2, wherein an image of the side walls of a bottle in one of said horizontal directions is projected on to said at least one device while the bottle is moving through a first position in the inspection station and an image of the side walls of the same bottle in another of said horizontal directions is projected on to said at least one device while the bottle is moving through another position in the inspection station.

* * * * *

UNITED STATES PATENT AND TRADEMARK OFFICE
CERTIFICATE OF CORRECTION

PATENT NO. : 4,367,405

DATED : January 4, 1983

INVENTOR(S) : Geoffrey Ewart Ford

It is certified that error appears in the above-identified patent and that said Letters Patent is hereby corrected as shown below:

On the title page Insert

-- (30) Foreign Application Priority Data
   October 13, 1977 (GB) United Kingdon   42553/77 --.

Signed and Sealed this

First Day of March 1983

[SEAL]

Attest:

GERALD J. MOSSINGHOFF

Attesting Officer      Commissioner of Patents and Trademarks